United States Patent [19]

Okumura et al.

[11] Patent Number: 6,037,393
[45] Date of Patent: Mar. 14, 2000

[54] COMPOUND, A PROCESS FOR THE PREPARATION THEREOF, AND A RESIN COMPOSITION

[75] Inventors: Koichi Okumura, Matsudo; Toshio Endo, Ohtake; Tomohisa Isobe, Iwakuni, all of Japan

[73] Assignee: Daicel Chemical Industries, Ltd., Sakai, Japan

[21] Appl. No.: 09/164,665

[22] Filed: Oct. 1, 1998

[51] Int. Cl.$^7$ .............................. C08K 5/34; C07D 249/16
[52] U.S. Cl. ............................................... 524/91; 548/257
[58] Field of Search ................. 524/91; 548/257

[56] References Cited

U.S. PATENT DOCUMENTS

| | | | |
|---|---|---|---|
| 5,032,498 | 7/1991 | Rody et al. | 430/512 |
| 5,319,090 | 6/1994 | MacLeay et al. | 548/257 |

FOREIGN PATENT DOCUMENTS

| | | |
|---|---|---|
| 0 057 160 | 8/1982 | European Pat. Off. . |
| 0 131 468 | 1/1985 | European Pat. Off. . |
| 60-038411 | 2/1985 | Japan . |
| 03 236390 | 10/1991 | Japan . |
| WO 96 29302 | 9/1996 | WIPO . |
| WO 97 35847 | 10/1997 | WIPO . |

*Primary Examiner*—Kriellion Sanders
*Attorney, Agent, or Firm*—Morgan & Finnegan, L.L.P.

[57] ABSTRACT

Novel polyester compounds having a benzotriazole group of the invention are obtained by a ring-opening addition-polymerisation of lactones with the alcoholic hydroxyl group of 3-(5-chloro-2H-benzotriazol-2-yl)-5-(1,1-dimethyl-ethyl)-4-hydroxy-benzene-propanol, 3-(2H-benzotriazol-2-yl)-4-hydroxy-benzene-ethanol, 3-(5-methyl-2H-benzotriazol-2-yl)-5-(1-methyl-ethyl)-4-hydroxy-benzene-propanolbis[3-(2H-benzotriazol-2-yl)-4-hydroxy-benzene-ethanol]methane or the like. These compounds are used as ultraviolet-rays absorbents for thermoplastic resins. The resulting resin composition has an excellent light resistance and chemical resistance.

5 Claims, 8 Drawing Sheets

COMPOUND, A PROCESS FOR THE PREPARATION THEREOF, AND A RESIN COMPOSITION

The present invention relates to new polyester compounds having a benzotriazole group and a preparation method thereof.

The present invention concerns also an ultraviolet-rays absorbent comprising one of the above-mentioned polyester compounds and a resin composition containing an ultraviolet absorbent which is very light resistant and chemical resistant.

Synthetic resins having a great strength, a great durability and that can be used in industrial mold processes are commonly used in various industrial fields, such as, for example, the car industry, electrical and electronical industries, or the construction industry. However, these synthetic resins have several drawbacks. When these synthetic resins are exposed to a light containing ultraviolet rays, such as sunlight, they are deteriorated by the ultraviolet rays and their colour changes. Consequently, the resulting reduction of their molecular weight leads to a drop in their strength.

In order to improve the resistance of these synthetic resins to ultraviolet rays, an ultraviolet-rays absorbent is usually added. For example, 2-(2'-hydroxy-5'-methyl-phenyl)benzotriazole, 5-chloro-2-(2'-hydroxy-3', 5'-di-tert-butyl-phenyl)benzotriazole or other benzotriazole like compounds and 2,4-dihydroxy-benzophenone, 2-hydroxy-4octyl-oxy benzophenone or other benzophenone-like compounds known as ultraviolet-rays absorbents.

However, these ultraviolet-rays absorbents used in the prior art have a low molecular weight and therefore a low-boiling point. Consequently, the addition of such compounds into synthetic resins involves various drawbacks. For example, when the ultraviolet-rays absorbent is added in a large amount, there is a phase separation between the synthetic resin and the ultraviolet-rays absorbent, thereby reducing the transparency of the synthetic resin and the mechanical strength thereof. Therefore, the amount of ultraviolet-rays absorbent to be added must be limited, if possible, to a small amount. However, in such a case, the light-resistance of the synthetic resin cannot be improved in a satisfactory way.

Moreover, during the mold process of the synthetic resin, the ultraviolet-rays absorbent is evaporated off or thermally deteriorated. The ultraviolet-rays absorbent leaks out of the surface of the molded articles. It is therefore impossible to confer a light-resistance to these synthetic resins which is stable for a long period of time.

In order to solve the above-mentioned drawbacks, there has been tried an attempt (JP-A-60-38411, JP-A-62181360 and JP-A-3-281685) that a group having a polymerizable double bond such as a vinyl group, is added to the above-mentioned ultraviolet-rays absorbents, and then it is polymerised to increase the molecular weight, whereby, compatibility with resins is improved and there are prevented evaporation, thermal decomposition and bleeding of the ultraviolet-rays absorbent.

However, the above-mentioned polymerizable ultraviolet-rays absorbents have the following drawbacks, therefore leaving the door open for further improvements. According to the type of the synthetic resin used, the compatibility of the resin and the ultraviolet-rays absorbent may not be sufficient, thereby decreasing the mechanical strength of the resin. This tendency is particularly remarkable in the case of a polyolefin, a polyvinyl-chloride, a polyvinylidene-chloride or other thermoplastic resins. Moreover, a long-term light resistance cannot be obtained.

Further, polyvinyl-chlorides, polyvinylidene-chlorides, polycarbonates, polyarnides, polyesters and other thermoplastic resins such as thermoplastic polyurethane resins have an extremely high mechanical strength and are widely used as a variety of materials in mold processes. However, polyvinyl-chlorides, polyvinylidene-chlorides, polycarbonates, polyesters, and thermoplastic urethane resins are degraded by alkaline compounds which reduce their mechanical strength. Resins such as polyamides are soluble in widely-used solvents such as methanol. Improvements regarding the resins' resistance to chemicals such as alkaline compounds and their solvent resistance have been therefore also required.

The inventors of the present invention have succeeded in obtaining ultraviolet-rays absorbents which are polymerizable compounds, by using, as starting materials, known ultraviolet-rays absorbents. The compatibility of these polymerizable compounds and the resin is excellent for a wide range of resins. The ultraviolet-rays absorbents of the invention confer an excellent light resistance to the resins without any loss of the desirable features of the resins. The ultraviolet-rays absorbents of the invention are not evaporated off or thermally deteriorated during the mold process and they do not leak out the molded articles. Thus, the inventors discovered how to obtain a synthetic resin having a light resistance stable for a long period of time. Moreover, the inventors discovered that an ultraviolet-rays absorbent containing the above-mentioned specified polymerizable compounds is able to confer an excellent resistance to alkaline compounds and an excellent solvent resistance, to a synthetic resin having a poor resistance to alkaline compounds and a poor solvent resistance. The present invention has been completed by the findings.

Formulae (1) and (1') show the polyester compounds provided by a first aspect of the present invention. These polyester compounds have a benzotriazole group.

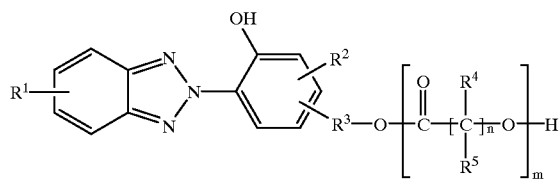

(1)

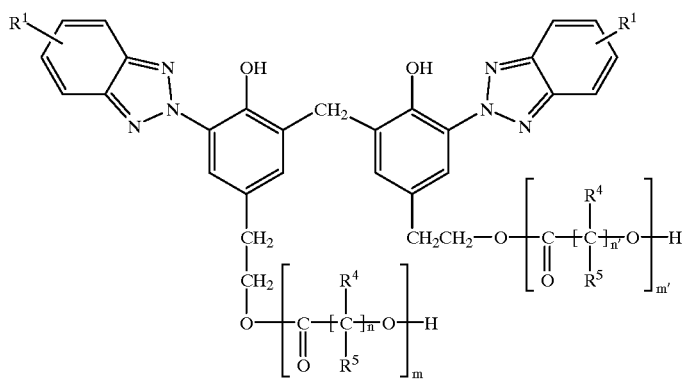

wherein:
R¹ is hydrogen atom, halogen atom or an alkyl group having 1 to 10 carbon atoms;
R² is hydrogen atom or an alkyl group having 1 to 10 carbon atoms;
R³ is an alkyl group having 1 to 10 carbon atoms;
R⁴ to R⁵ are hydrogen atoms or an alkyl group having 1 to 10 carbon atoms;
n is an integer of 4–8;
m is a number of 1–20.

A second aspect of the present invention also provides a method for preparing the above-mentioned polyester compounds containing a benzotriazole group described in the first aspect of the invention. According to the second aspect of the present invention, these polyester compounds may be obtained by polymerising the compounds of formulae (2) and (2') with a lactone compound of formula (3). This polymerisation reaction is a ring-opening addition-polymerisation of the lactone compound.

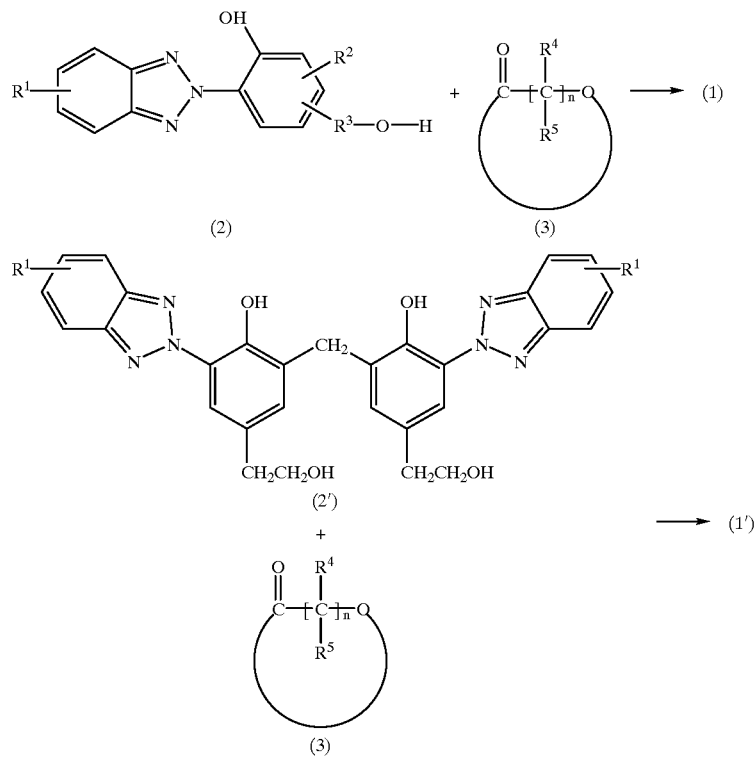

wherein:
R¹ is hydrogen atom, halogen atom or an alkyl group having 1 to 10 carbon atoms;
R² is hydrogen atom or an alkyl group having 1 to 10 carbon atoms;
R³ is an alkyl group having 1 to 10 carbon atoms;
R⁴ to R⁵ are a hydrogen atom or an alkyl group having 1 to 10 carbon atoms;
n is an integer of 4–8;
m is a number of 1–20.

A third aspect of the present invention also provides ultraviolet-rays absorbents comprising the above-mentioned polyester compounds containing a benzotriazole group described in the first aspect of the present invention.

Further, a fourth aspect of the present invention provides synthetic-resin compositions containing a synthetic resin and the above-mentioned ultraviolet-rays absorbents described in the third aspect of the invention.

The resin compositions of a fifth aspect of the invention comprise, as a synthetic resin, at least one synthetic resin selected from the group consisting of a polyvinyl-chloride, a polyvinylidene-chloride, a polyolefin, a polycarbonate, a polystyrene, an acrylic resin, a methacrylic resin, a polyamide, a polyester, an acrylonitrile-butadiene-styrene resin or a thermoplastic urethane resin.

The resin compositions according to the invention have a high and time-stable light resistance and chemical resistance.

Figure 1:
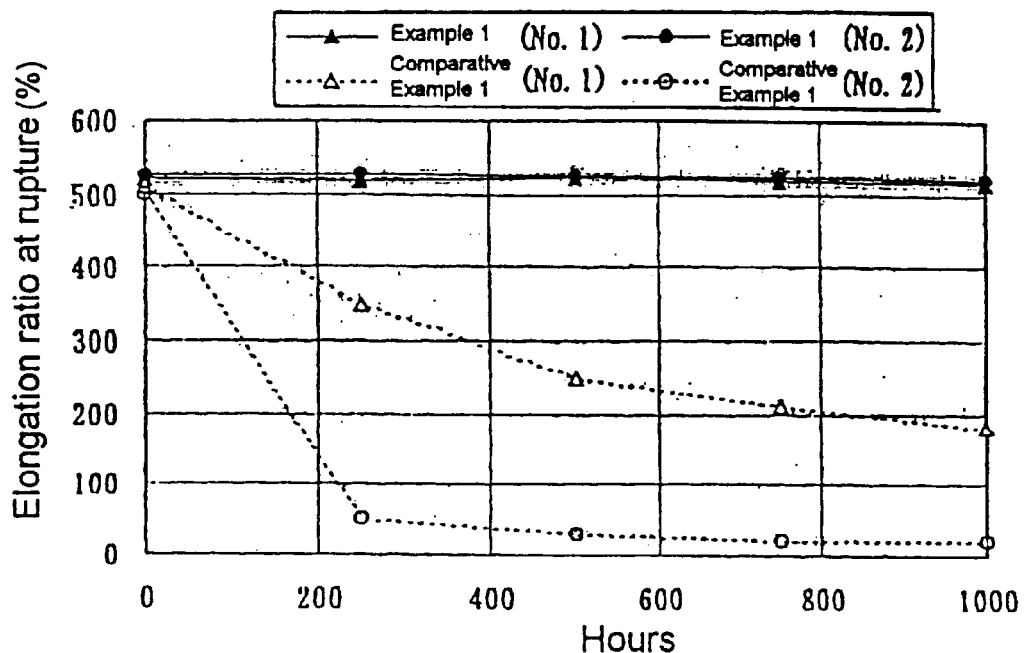
FIG. 1 is a graph showing the elongation ratio at rupture, after a light-exposure test, of the products of the prior art (Comparative Example 1) and the products of the present invention (Example 1), respectively.

The polyester compounds containing a benzotriazole group of the above-mentioned formulae (1) and (1') of the present invention are novel compounds and may be used as ultraviolet-rays absorbents for synthetic resins.

The method of preparing the above-mentioned compounds having a benzotriazole group represented by the above-mentioned formula (1) or (1') is a ring-opening addition-polymerisation of the lactone compound (3) of formula (3) with one of the alcohols of formulae (2) and (2').

In the above-mentioned formulae (1) and (1'), m is an integer which indicates the number of molecules of each polymer. However, regarding the whole polymer, m is not necessarily an integer. When the values of m or m' are less than 1 in the whole polymer, the ultraviolet-rays absorbent tends to leak-out of the surface of the molded articles. On the contrary, when the values of m or m' are greater than 20, the ultraviolet-rays absorbability is unpreferably insufficient. However, regarding the ultraviolet-rays absorbents of formulae (1) and (1'), m and m' are not limited to the above-mentioned values.

The alcohols of formula (2) may be, specifically, 3-(5-chloro-2H-benzotriazol-2-yl)-5-(1,1-dimethyl-ethyl)-4-hydroxy-benzene-propanol3-(2H-benzotriazol-2-yl)-4-hydroxy-benzene-ethanol, 3-(5-methyl-2H-benzotriazol-2-yl)-5-(1-methyl-ethyl)-4-hydroxy-benzene-propanol or the like.

The alcohols of formula (2') may be, for example, bis-[3-(2H-benzotriazol-2-yl)-4-hydroxy-benzene-ethanol] methane or the like. In formula (2') the two benzotriazole rings may be substituted by the group $R^1$ of formula (2). These two benzotriazole rings may be substituted by similar $R^1$ groups or by different $R^1$ groups.

In the formulae (2) and (2'), ethanol, propanol or other alcohols which substitute the benzene ring may be linear alcohols or branched alcohols.

The above-mentioned alcohols may be synthetic products or tradely available products. Otherwise, they can be obtained by reducing tradely-available benzotriazole-type ultraviolet-rays absorbents by using lithium-aluminium hydride, etc.

ε-caprolactone, trimethyl-ε-caprolactone, monomethyl-ε-caprolactone, γ-butyrolactone, δ-valerolactone, or the like, may be used as the lactone compound of the above-mentioned formula (3).

The catalysts that may be used for the ring-opening addition-polymerisation are, for example, tetraethyl-titanate, tetrabutyl-titanate, tetrapropyl-titanate, or other organic titanate-compounds, stannous octoate, dibutyl-tin-oxide, dibutyl-tin-dilaurate, a n-butyl-tin tris(alkanoate) or other organic tin-compounds, stannous chloride, stannous bromide, stannous iodide or other stannous halide compounds.

The amount by weight of catalyst added is 0.1–10,000 ppm and preferably 1–5,000 ppm based on the amount by weight of alcohol used. When the amount of catalyst is less than 0.1 ppm, the ring-opening reaction of the lactones is remarkably slown down which is not economically interesting. On the contrary, when the amount of catalyst is more than 10,000 ppm, the ring-opening reaction occurs quickly but when the obtained polyester compounds containing a benzotriazole group are used to form synthetic resins, these resins have a poor durability and a poor water resistance.

The reaction temperature is 90° C.–240° C. and preferably 100° C.–220° C.

When the reaction temperature is less than 90° C., the ring-opening reaction of the lactones is remarkably slown down which is not economically interesting. On the contrary, when the reaction temperature is more than 240° C., the polylactones obtained by ring-opening addition-polymerisation are depolymerized which is not desirable. Moreover, when the reaction is performed under an inert gas atmosphere, such as a nitrogen gas atmosphere, particularly good results regarding the colour of the final product can be obtained.

The polyester compounds containing a benzotriazole group of the invention may be synthesised according to the aforementioned method. According to the present invention, the synthetic resins that can be synthesised by adding in a resin, as an ultraviolet absorbent, the polyester compounds containing a benzotriazole group of the invention (hereinafter, referred as to ultraviolet-rays absorbable compounds or ultraviolet-rays absorbable polymers), as a ultraviolet-rays absorbable compound, to a resin, are not limited. Any type of known resin may be used. However, the thermoplastic resins are the most suitable because it is very easy to add the polyester compounds containing a benzotriazole group of the invention thereinto.

The thermoplastic resins that may be used are, for example, a polyvinyl-chloride, a polyvinylidene-chloride, a polyolefin, a polycarbonate, a polystryrene, an acrylic resin, a methacrylic resin, a polyamide, a polyester, an acrylonitrile-butadiene-styrene resin (ABS), a thermoplastic polyurethane resin, a copolymer of vinyl-chloride and vinylidene-chloride-acrylonitrile resin, an acrylonitrile-styrene resin (AS), a vinyl-acetate resin, a polyphenylene-ether, a polysulphone, a polyether sulphone, a polyether-ether-ketone or other crystalline plastics. Preferably, a polyvinyl-chloride, a poly-vinylidene-chloride, a polyolefin, a polycarbonate, a polystyrene, an acrylic resin, a meth-acrylic resin, a polyamide, a polyester, an ABS resin and a thermoplastic urethane resin may be, for example, used.

Among them, more preferably and, for example, a polyvinyl-chloride, a polyvinylidene-chloride, a polycarbonate, a polyester, a thermoplastic urethane or other thermoplastic resin having a poor alkali resistance and a polyamide or other thermoplastic resin having a poor solvent resistance may be used. According to the present invention, one, two or more kinds of resin may be used.

According to the present invention, the relative proportions of the resin and the ultraviolet-rays absorbent of formulae (1) and (1') are not limited. However, usually, the proportions are, in weight ratio: (resin(s) amount (amount by weight): ultraviolet-rays absorbent (amount by weight) 80–99.995:20–0.005 and more preferably, 90–99:10–0.1.

The resin compositions of the invention may also optionally contain at least one sort of the following known additives: antioxidants, photostabilisers, process stabilisers, anti-aging agents and compatibilizing agents.

The anti-oxidants that can be used are, for example, bis-[3-(3,5-di-tert-butyl-4-hydroxyphenyl) propionyl]1, 6 hexane-diol, 3,5-di-tert-butyl-4-hydroxy-benzyl-phosphonate-diethyl ester or other hindered phenol type anti-oxidants, dilauryl-3,3'-dithio-dipropionate or other organic sulphuric anti-oxidants, trialkyl-phenyl-phosphate or other phosphorous-containing anti-oxidants.

As the photostabiliser, for example, bis-(2, 2, 6, 6-tetramethyl-4-piperidyl)sebacate or other hindered-amine photo-stabilisers may be used, as well as dibutyl-dithio-nickel-carbamate or other salts of nickel.

As the process stabiliser, for example, tris-(2, 4-di-tert-butyl phenyl)phosphite or other phosphorous-containing process stabilisers may be used.

The anti-aging agents may be, for example, 1, 1-bis-(4-hydroxy phenyl)cyclohexene, N,N'-diphenyl-p-phenylene-diamine or the like.

The compatibilizing agents may be, for example, a block copolymer of styrene-butadiene-styrene, a block copolymer of styrene-ethylene butylene-styrene or other thermoplastic rubbers.

The amount of these additives is not limited but usually, it represents about , 0.01 to 20 weight % based on the synthetic resin.

The compositions of the invention can be employed in all uses in which the synthetic resin can be employed. Preferably, the resins of the invention may be used when there are risks in being exposed to a light such as sunlight and ultraviolet rays. Specifically, this means that they can be used as glass-substitute products or as glass coating, for houses, equipment, for windows of means of transport, as a coating for lighting glass and for light-sources protecting glass, as an internal or external painting for means of transport, as a material to produce light sources such as florescent lamps or mercury lamps which emit ultraviolet-rays, for producing precise devices, as a material for electrical or electronic devices, As a material for cutting-off electromagnetic waves or the like which are generated by a variety of displays, for food, for chemicals, pharmaceuticals, as a coating or a container of pharmaceuticals. The compositions of the present invention may be used to produce sheets or films that may be used in the agricultural field. The compositions of the present invention may be used for printing materials, such as colorants, in cosmetics for preventing fading, in creams for stopping sunburn, in shampoos or rinses, or other hair care products, in sponge wears, stockings, for making fibres used to manufacture clothes or other articles such as hats or the like, curtains, carpets, for furniture such as wall paper, for plastic lenses, contact lenses, artificial eyes or other medical devices, optical filters, prisms, mirrors, optical articles for photographic material, tapes, ink or other stationery articles, for marker boards, or as a coating for the surface of marking devices.

Although, the present invention will be further explained with reference to the following Synthesis Examples (preparation of an ultraviolet-rays absorbent) Examples (preparation of a synthetic-resin composition) and Comparative Examples, the present invention is not limited by those. It is to be noted that the term % used hereinafter is a % by weight (wt %), unless specified otherwise.

(i) Light-exposure test

The device used is a dew-cycle sunshine weather-meter WEL-SUN-DC manufactured by Suga Shikenki CO., Ltd. The light source used is a carbon arc with a raining cycle of 18 min per 120 min. The temperature of the black panel was set at 80° C.

(ii) Elongation at rupture test

The device used is a Shimadzu Autograph DSC of Shimadzu CO., Ltd. The measurement conditions were: 200 kg/FS, cross-head speed=50 mm/min, GL=30 mm.

At first, we will describe the ultraviolet-rays absorbent of the formula 1.

SYNTHESIS EXAMPLE 1

134.5 g of 3-(2H-benzotriazol-2-yl)-4-hydroxybenzene-ethanol (trade name "JF-269", produced by Johoku Kagaku Co., Ltd.) were placed in a glass flask equipped with a condenser, a nitrogen introducing-tube, a thermometer and a stirrer. 342 g of $\epsilon$-caprolactone and 50 ppm of a n-butyl-tin tris(alkanoate) (trade name "SCAT-24" produced by Sankyo Yukigosei Co.; Ltd) were then added in the above-mentioned flask. The reaction temperature was set at 150° C. for 6 hours and the concentration of the $\epsilon$-caprolactone was then measured during the reaction by gas chromatography. When the concentration of the $\epsilon$-caprolactone was equal to 0.45%, the reaction was stopped. The reacting product showed an acid value of 1.9 mg KOH/g and was solid at room temperature.

The infrared-absorption spectrum of the obtained compound (1) was measured. This compound showed an absorption peak at the specific absorption wavelengths of the 3-(2H-benzotriazol-2-yl)-4-hydroxy-benzene-ethanol which are 1460, 1257, 1217, 870, 748 cm$^{-1}$ and at the specific absorption wavelengths of the polycaprolactone which are 2941, 2864 and 1257 cm$^{-1}$.

The $^1$H-NMR spectrum of the obtained compound (1) was also measured to verify the structure thereof. This $^1$H-NMR spectrum showed a signal at 7.5 ppm (corresponding integrated value A1) and a signal at 7.9 ppm (corresponding integrated value A2) both of these signals corresponding to the aromatic protons of the benzotriazole ring. The signal at 2.3 ppm corresponds to the methylene protons near the carbon atoms of the polycaprolactone and had a corresponding integration B. Since the value of (B/(A1+A2)) was equal to 3, the structure of the compound (1) could be verified.

10 mg of the compound (1) were dissolved into 50 ml of chloroform to measure the ultraviolet-rays absorption spectra of the compound (1) using a quartz cell having a light-path length of 1 mm. The compound (1) had absorption peaks at 220 nm (intensity 0.98), 300 nm (intensity 0.51) and 350 nm (intensity 0.58). The strong absorption intensities showed that the compound (1) had a sufficient ultraviolet-rays absorption in the ultraviolet region.

SYNTHESIS EXAMPLE 2

As mentioned above, in Example 1, 570 g of ε-caprolactone and 50 ppm of a n-butyl-tin tris(alkanoate) (trade name "SCAT-24" produced by of Sankyo Yukigosei Co. Ltd;) were added in 134.5 g of 3-(2H-benzotriazol-2-yl)-4-hydroxy-benzene-ethanol (trade name "JF-269" produced by Johoku Kagaku CO,. Ltd;). After 8 hours while maintaining the reaction temperature at 150° C., the concentration of the ε-caprolactone in the reaction mixture was measured by gas chromatography. The reaction was stopped when the concentration of ε-caprolactone was equal to 0.30%. The resulting product was a solid at room temperature and showed an acid value corresponding to 2.05 mg KOH/g.

The infrared-absorption spectrum of the obtained compound (2) was measured at the same specific absorption wavelengths as in the case of compound (1). This compound (2) had an infrared-absorption at the specific absorption wavelengths of the 3-(2H-benzotriazol-2-yl)-4-hydroxy-benzene-ethanol and at the specific absorption wavelengths of the polycaprolactone.

Further, it was confirmed that an analysis by $^1$H-NMR shows that it has aromatic-ring protons in the benzotriazole ring and methylene protons adjacent to carbonyl carbon in the polycaprolactone, and that the integrated ratio (B/(A1+A2)) is 5, resulting in that it is the compound of the structure (2).

The ultraviolet-rays absorption spectra of this compound (2) was measured as for the compound (1). The compound (2) had absorption peaks at 220 nm (intensity 0.82), 300 nm (intensity 0.39), and 350 nm (intensity 0.42). The strong intensities showed that the compound (2) had a sufficient ultraviolet-rays absorption in the ultraviolet region.

EXAMPLE 1 AND COMPARATIVE EXAMPLE 1

The ultraviolet-rays absorbable polymers of the invention and the ultraviolet-rays absorbents of the prior art were mixed with 100 parts by weight of polypropylene. Table 1 shows the parts by weight of the ultraviolet-rays absorbents with respect to 100 parts by weight of polypropylene. The resulting resin was injection-molded to form a dumbbell of JIS N°2.

TABLE 1

|  |  | Ultraviolet-rays absorbent | parts by weight |
|---|---|---|---|
| Example 1 | N°1 | compound synthesized in Synthesis Example 1 | 2 |
|  | N°2 | compound synthesized in Synthesis Example 2 | 2 |
| Comparative Example 1 | N°1 | trade name "JF-269" | 2 |
|  | N°2 | none | 0 |

The obtained dumbbells were submitted to the light-exposure test using the above-mentioned sunshine weathermeter. After a determined time of exposure, a resistance test was performed to determine the corresponding elongation ratio at rupture.

The experimental conditions were explained hereinafter. FIG. 1 shows the corresponding elongation ratio at rupture. According to FIG. 1, it was confirmed that the compositions containing the ultraviolet-rays absorbable polymers of the present invention have an excellent light resistance compared to the compositions containing the ultraviolet-rays absorbents of the prior art.

EXAMPLE 2 AND COMPARATIVE EXAMPLE 2

The ultraviolet-rays absorbable compounds obtained in the above-mentioned Synthesis Examples and the ultraviolet-rays absorbents of the prior art were mixed with 100 parts by weight of polyvinyl-chloride. Table 2 shows the parts by weight of the ultraviolet-rays absorbents with respect to 100 parts by weight of polyvinyl-chloride. The resulting resin was then injection-molded to form a plain plate having a thickness of 1.6 mm. The resulting plain plate was then submitted to the light-exposure test. The results are collectively shown in Table 2.

TABLE 2

|  |  | Ultraviolet-rays absorbent | parts by weight | light - exposure test |
|---|---|---|---|---|
| Example 2 | N°1 | compound of Synthesis Example 1 | 1 | no color change after 2000 hours |
|  | N°2 | compound of Synthesis Example 2 | 1 | no color change after 2000 hours |
| Comparative Example 2 | N°1 | trade name "JF-269" | 1 | color change after 1000 hours |
|  | N°2 | none | 0 | color change after 600 hours |

EXAMPLE 3 AND COMPARATIVE EXAMPLE 3

The ultraviolet-rays absorbable compounds obtained in the above-mentioned Synthesis Examples and the ultraviolet-rays absorbents of the prior art were mixed with 100 parts by weight of polyvinylidene-chloride. Table 3 shows the parts by weight of the ultraviolet-rays absorbents with respect to 100 parts by weight of polyvinylidene-chloride. The resulting mixture was then injection-molded to form a plain plate having a thickness of 1.6 mm. The resulting plain plates were then submitted to the light-exposure test. The results are shown in Table 3.

TABLE 3

| | | Ultraviolet-rays absorbent | parts by weight | light-exposure test |
|---|---|---|---|---|
| Example 3 | N°1 | compound obtained in Synthesis Example 1 | 1 | no color change after 2000 hours |
| | N°2 | compound obtained in Synthesis Example 2 | 1 | no color change after 2000 hours |
| Comparative Example 3 | N°1 | trade name "JF-269" | 1 | color change after 800 hours |
| | N°2 | none | 0 | color change after 400 hours |

EXAMPLE 4 AND COMPARATIVE EXAMPLE 4

The ultraviolet-rays absorbable compounds obtained in the above-mentioned Synthesis Examples and the ultraviolet-rays absorbents of the prior art were mixed with 100 parts by weight of polystyrene. Table 4 shows the parts by weight of the ultraviolet-rays absorbents with respect to 100 parts by weight of polystyrene. The resulting mixtures were then injection-molded to form plain plates having a thickness of 1.6 mm.

TABLE 4

| | | Ultraviolet-rays absorbent | parts by weight |
|---|---|---|---|
| Example 4 | N°1 | compound of Synthesis Example 1 | 1 |
| | N°2 | compound of Synthesis Example 2 | 1 |
| Comparative Example 4 | N°1 | trade name "JF-269" | 1 |
| | N°2 | none | 0 |

Figure 2:
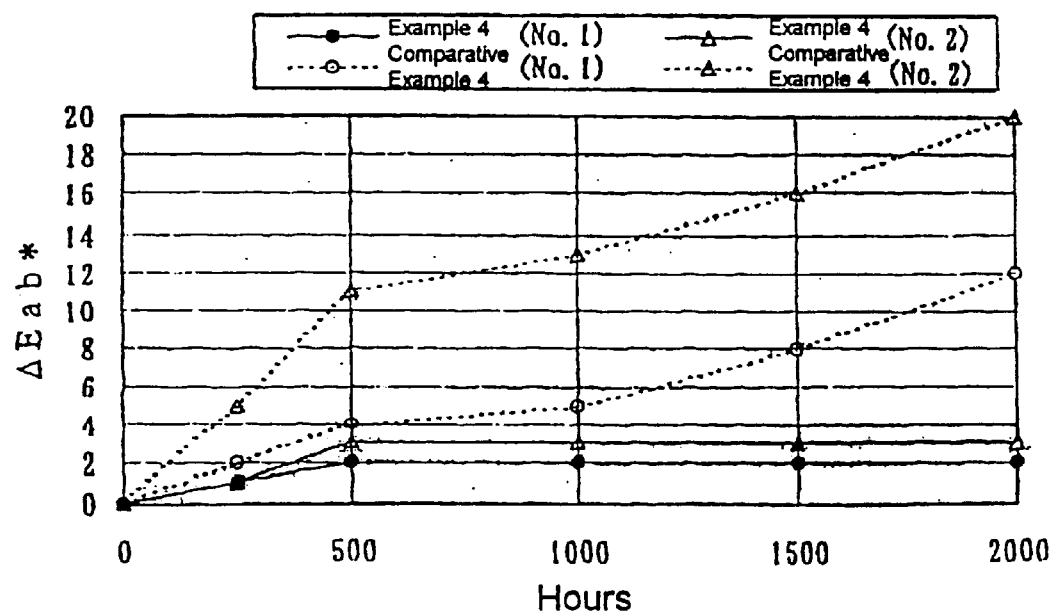
FIG. 2 is a graph showing the colour difference ($\Delta Eab^*$), after a light-exposure test, of the products of the prior art (Comparative Example 4) and the products of the present invention (Example 4), respectively.

The obtained plain plates were then submitted to the light-exposure test as in Example 1. The difference of colour (ΔEab*) between the colour of the plain plate before the exposure and the colour of the plain plate after the exposure was measured by a colorimeter (Colour Computer SM-2 manufactured by Suga Shikenki CO., Ltd.). FIG. 2 shows the results of this measurements. According to FIG. 2, it was confirmed that the present invention products have an excellent light resistance compared to the products of the prior art.

EXAMPLE 5 AND COMPARATIVE EXAMPLE 5

The ultraviolet-rays absorbable compounds obtained in the above-mentioned Synthesis Examples and the ultraviolet-rays absorbents of the prior art were mixed with 100 parts by weight of a copolymer of acrylonitrile-butadiene-styrene. Table 5 shows the parts by weight of the ultraviolet-rays absorbents with respect to 100 parts by weight of the acrylonitrile-butadiene-styrene copolymer. The resulting mixtures were then injection-molded to form plain plates having a thickness of 1.6 mm.

TABLE 5

| | | Ultraviolet-rays absorbent | parts by weight |
|---|---|---|---|
| Example 5 | N°1 | compound of Synthesis Example 1 | 1 |
| | N°2 | compound of Synthesis Example 2 | 1 |
| Comparative Example 5 | N°1 | trade name "JF-269" | 1 |
| | N°2 | none | 0 |

Figure 3:
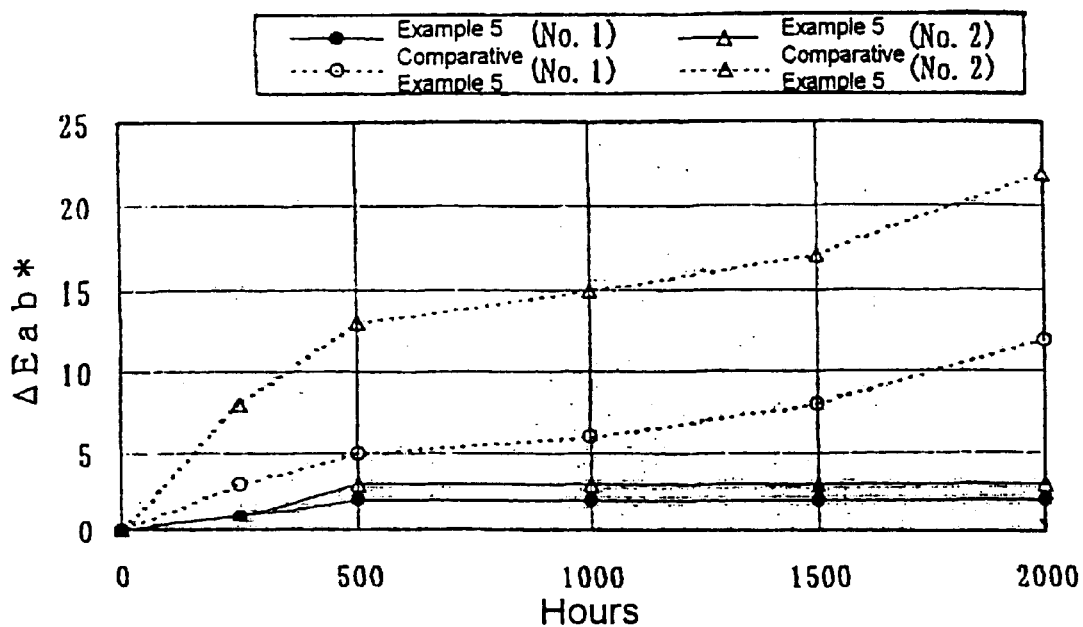
FIG. 3 is a graph showing the colour difference ($\Delta Eab^*$), after a light-exposure test, of the products of the prior art (Comparative Example 5 5) and the products of the present invention (Example 5), respectively.

The obtained plain plates were then submitted to the light-exposure test as in Example 1. The difference of colour (ΔEab*) between the colour of the plain plate before the exposure and the colour of the plate after the exposure was measured by a calorimeter (Colour Computer SM-2 manufactured by Suga Shikenki CO., Ltd.). FIG. 3 shows the results of these measurements. According to FIG. 3, the products of the present invention have an excellent light resistance compared to the products of the prior art.

EXAMPLE 6 AND COMPARATIVE EXAMPLE 6

The ultraviolet-rays absorbable compounds obtained in the above-mentioned Synthesis Examples and the ultraviolet-rays absorbents of the prior art were mixed with 100 parts by weight of a polycarbonate. Table 6 shows the parts by weight of the ultraviolet-rays absorbents with respect to 100 parts by weight of the polycarbonate. The resulting mixtures were then injection-molded to form plain plates having a thickness of 1.6 mm.

TABLE 6

| | | Ultraviolet-rays absorbent | parts by weight |
|---|---|---|---|
| Example 6 | N°1 | compound of Synthesis Example 1 | 1 |
| | N°2 | compound of Synthesis Example 2 | 1 |
| Comparative Example 6 | N°1 | trade name "JF-269" | 1 |
| | N°2 | none | 0 |

Figure 4:
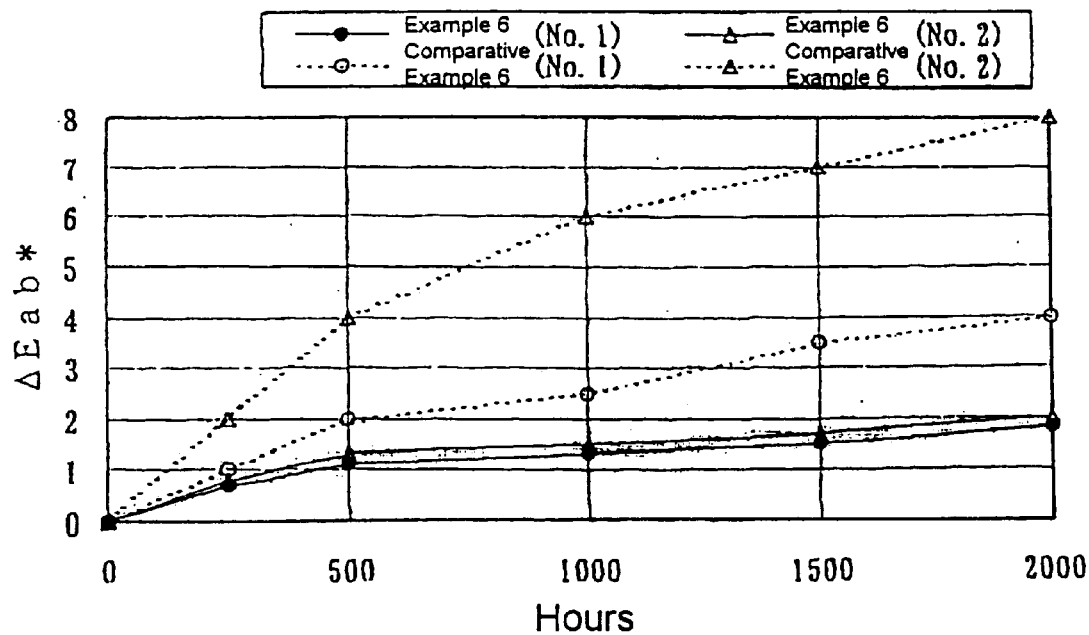
FIG. 4 is a graph showing the colour difference ($\Delta Eab^*$), after a light-exposure test, of the products of the prior art (Comparative Example 6) and the products of the present invention (Example 6), respectively.

The obtained plain plates were submitted to the light-exposure test as in Example 1. The difference of colour (ΔEab*) between the colour of the plain plate before the exposure and the colour of the plain plate after the exposure was measured by a colorimeter (Colour Computer SM-2 manufactured by Suga Shikenki CO., Ltd.). FIG. 4 shows the results of these measurements. According to FIG. 4, the products of the present invention have an excellent light resistance compared with the products of the prior art.

EXAMPLE 7 AND COMPARATIVE EXAMPLE 7

The ultraviolet-rays absorbable compounds obtained in the above-mentioned Synthesis Examples and the ultraviolet-rays absorbents of the prior art were mixed with polystyrene and dissolved in tetrachloro-ethane to form a homogenous solution. Table 7 shows the amounts by weight of the ultraviolet-rays absorbents and the polystyrene, respectively. The resulting solution was dropped on a quartz-glass disk having a thickness of 1 mm and a diameter of 30 mm. A thin homogenous film having a thickness of 0.9–1.0 μm was then formed by use of a spin coater. The resulting disk was introduced in 70° C. hot water and the film absorbance at 340 nm was measured every two hours.

In the case of the ultraviolet-rays absorbent of the prior art (Comparative Example 7), the absorbance linearly decreased because of the elution of the ultraviolet-rays absorbent. On the contrary, in the case of the compound synthesised in Example 1 (Example 7, ultraviolet-rays absorbent of the invention), there was no elution or bleeding of the ultraviolet-rays absorbent and the absorbance kept the same value as it was initially. Table 7 shows the initial absorbance at 340 nm ($A_0$) and the absorbance at 340 nm after 10 hours ($A_{10}$). The ratio $A_0/A_{10}$ is also indicated in Table 7.

TABLE 7

| | Ultraviolet-rays absorbent | parts by weight (mg) | up:A0 down:A10 | retention rate (%) |
|---|---|---|---|---|
| Example 7 | compound obtained in Synthesis Example 1 polystyrene | 100 900 | 0.320 0.318 | 99.3 |
| Comparative Example 7 | trade name "JF-269" polystyrene | 100 900 | 0.325 0.205 | 63.1 |

After 10 hours, the disk was submitted to the light-exposure test as explained in Example 1. The disk obtained in Example 7 was exposed for 500 hours without any eye-visible colour change. However, the disk obtained in Comparative Example 7 showed yellowing after 200 hours of light exposure. Consequently, it is confirmed that the compositions of the invention have a stable light resistance.

EXAMPLE 8 AND COMPARATIVE EXAMPLE 8

The ultraviolet-rays absorbable compounds obtained in the above-mentioned Synthesis Example 2 and the ultraviolet-rays absorbents of the prior art were mixed with poly(methyl methacrylate) (PMMA) and dissolved in tetrachloroethane to form a homogenous solution. Table 8 shows the amount by weight of the ultraviolet-rays absorbent and the PMMA, respectively. The resulting solution was used, as in Example 7, to form a homogeneous film having a thickness of about 1 μm. The resulting disk was introduced in 70° C. hot water and its absorbance at 340 nm was measured every two hours. Table 8 shows the corresponding results.

TABLE 8

| | Ultraviolet-rays absorbent | parts by weight (mg) | up:A0 down:A10 | retention rate (%) |
|---|---|---|---|---|
| Example 8 | compound obtained in Synthesis Example 1 PMMA | 150 850 | 0.468 0.458 | 97.9 |
| Comparative Example 8 | trade name "JF-269" PMMA | 100 900 | 0.430 0.055 | 12.8 |

On the basis of the results shown in Table 8, it can be proved that the ultraviolet-rays absorbable polymers of the invention are completely fixed inside the matrix of the resin and consequently there is quite no elution and no bleeding of the ultraviolet-rays absorbable polymers of the invention.

EXAMPLE 9 AND COMPARATIVE EXAMPLE 9

15 mg of the ultraviolet-rays absorbable polymer obtained in synthesis Example 2 were mixed with 85 mg of polyethylene terephthalate (Example 9) and 5 mg of a ultraviolet-rays absorbent of the prior art (in the present case, 2-(2'-hydroxy-5'-methyl-phenyl)benzotriazole) were mixed with 95 mg of polyethylene terephthalate (Comparative Example 9). These mixtures were used to form films as in Example 7. The obtained films were introduced into a 2% sodium hydroxide aqueous solution at 70° C. The absorbance (At) of these films was measured at 340 nm and 231 nm every two hours. The retention ratio was defined as At/Ao. After 10 hours, the absorbance and the retention ratio of the films were measured. In the case of the polyethylene terephthalate films without any ultraviolet-rays absorbent, there was a remarkable dissolution of the polyethylene terephthalate film (there was a decrease of 50% of the retention ratio 231 nm). In the case of the polyethylene terephthalate film containing a ultraviolet-rays absorbent of the prior art, there was also a remarkable elution of the ultraviolet-rays absorbent (there was a decrease of 85% of the retention ratio at 340 nm) in addition to the above-mentioned dissolution of the film. However, the retention ratio was always maintained to about 100% in the case of Example 9.

The ultraviolet-rays absorbent of formula (1') will be described below.

SYNTHESIS EXAMPLE 3

170.3 g of ε-caprolactone and 50 ppm of a n-butyl-tin tris(alkanoate) (trade name "SCAT-24" manufactured by Sankyo Organic Synthesis Co., Ltd) were added into a flask provided with a condenser, a nitogen introducing-tube, a thermometer and a stirrer, containing 129.3 g of bis-[3-(2H-benzotriazol-2-yl)-4-hydroxy-benzene-ethanol]methane (trade name "MBEP" manufactured by Otsuka Kagaku CO. Ltd.). The reaction mixture was kept at a temperature of 150° C. for 6 hours. The concentration of the ε-caprolactone of the reaction mixture was measured by gas chromatography. The reaction was stopped when the concentration of ε-caprolactone was equal to 0.43%. The resulting product was liquid at room temperature and had an acid value corresponding to 1.8 g KOH/g and a viscosity of 2645 $10^3$Pa.s (2645 cPo) at 60° C. This product had an average molecular weight by number (MN) of 1391 and an average molecular weight by mass of 1688, both measured by a GPC analysis. The ratio MW/MN was equal to 1.213.

Figure 5:
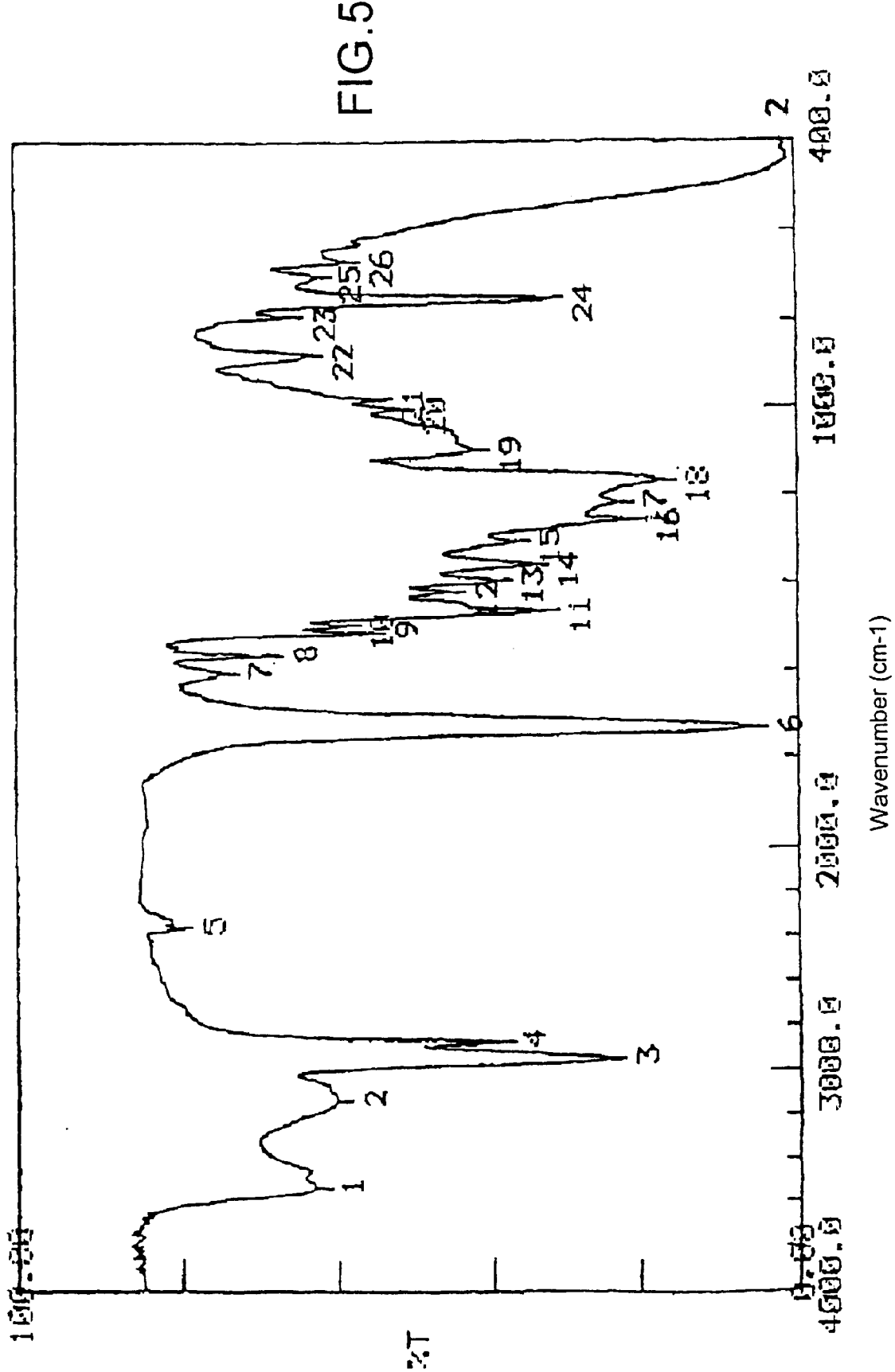
FIG. 5 shows the infrared-absorption spectrum of the compound (3) 10 obtained in Synthesis Example 3.
Figure 6:
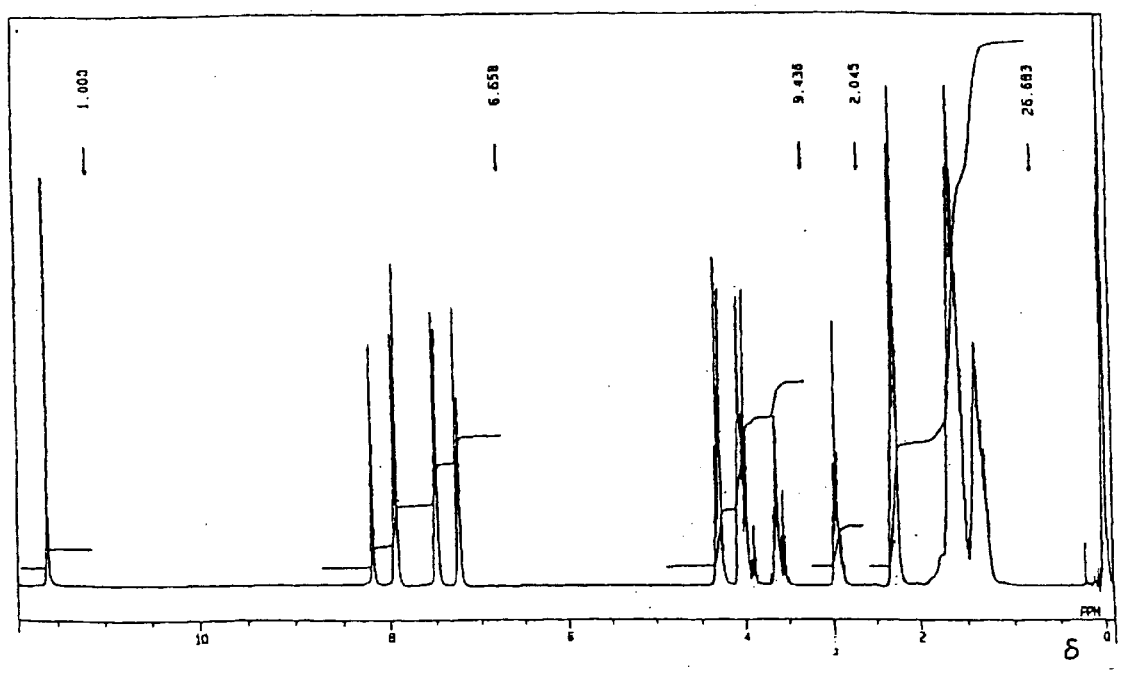
FIG. 6 is the $^1$H-NMR spectrum of the compound (3) obtained in Synthesis Example 3.
Figure 7:
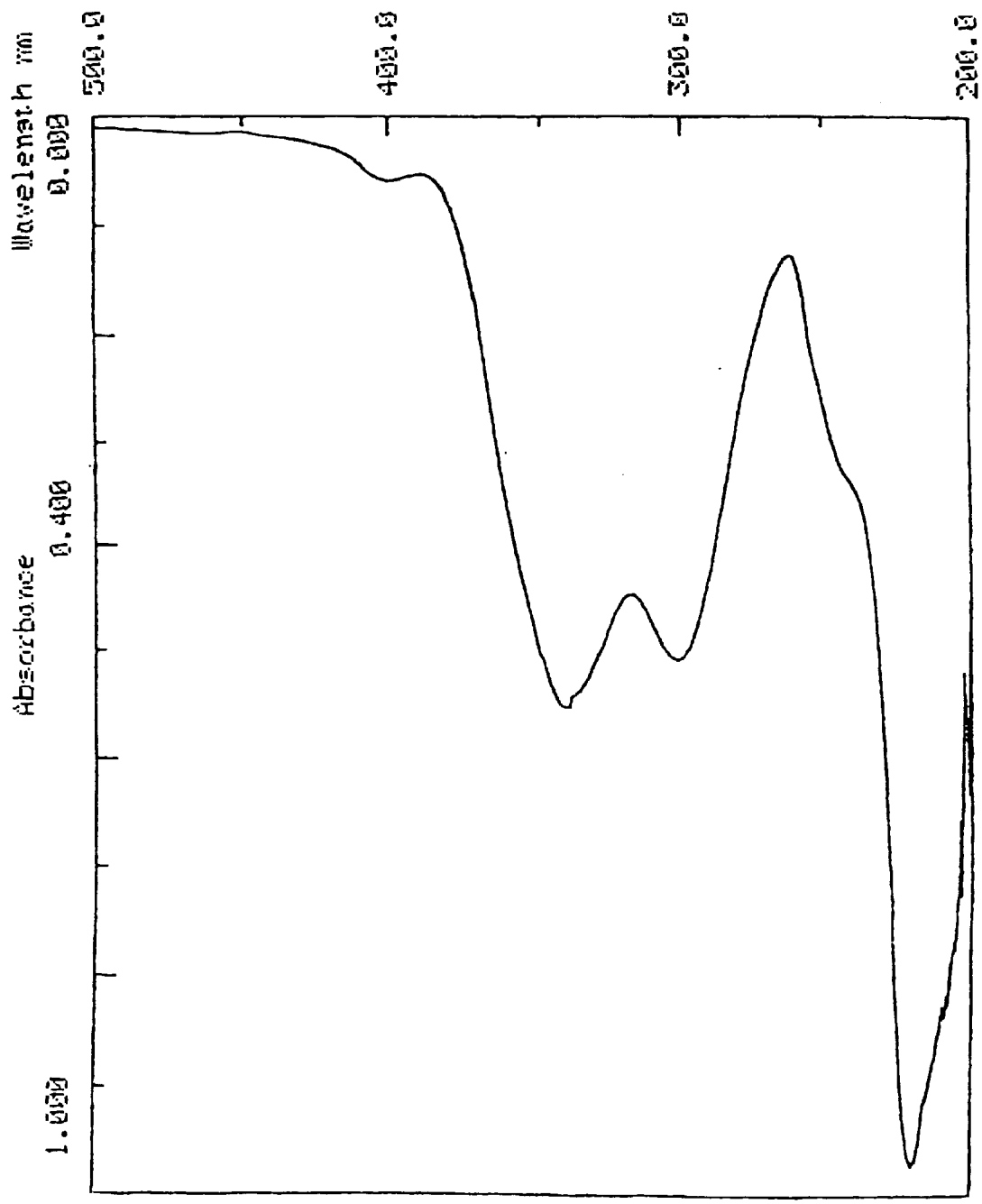
FIG. 7 is the ultraviolet and visible light-absorption spectrum of the compound (3) obtained in Synthesis Example 3.

FIG. 5 shows the infrared spectrum of the obtained compound (3). FIG. 6 shows the $^1$H-NMR spectrum of the same compound. 10 mg of compound (3) were dissolved in 50 ml of chloroform. The ultraviolet-rays absorption spectrum of this compound was then measured using a quartz cell having a light-pathway of 1 mm length. FIG. 7 shows the results of this experiment. According to FIG. 7, the compound (3) has a sufficient ultraviolet-rays absorption in the ultraviolet range.

SYNTHESIS EXAMPLE 4

206.3 g of ε-caprolactone and 50 ppm of a n-butyl-tin tris(alkanoate) (trade name: "SCAT-24", produced by Sankyo Organic Synthesis Co., Ltd.) were added into a flask similar to the flask mentioned in Synthesis Example 3 containing 93.7 g of bis-[3-(2H-benzotriazol-2-yl)-4-hydroxy-benzene-ethanol]methane (trade name "MBEP", produced by Oozuka Chemicals Co., Ltd.). The reaction mixture was kept at a temperature of 150° C. for 6 hours. The concentration of ε-caprolactone of the reaction mixture was measured by gas chromatography. The reaction was stopped when the concentration of ε-caprolactone was equal to 0.55%. The resulting product was solid at room temperature and had an acid value corresponding to 2.5 mg KOH/g and a viscosity of 987 $10^3$Pa.s (987 cPo) at 60° C. This product had an average molecular weight by number (MN) of 2017 and an average molecular weight by mass (MW) of 2465, both measured by a GPC analysis. The ratio MW/MN was equal to 1.222.

The infrared-absorption spectrum of the obtained compound (4) showed that this compound (4) had the infrared-absorption peaks corresponding to the specific infrared-absorption peaks of the bis-[3-(2H-benzotriazol-2-yl)-4-hydroxy-benzene-ethanol]methane (at wavelengths of 1460, 1257, 1217, 870, 748 cm$^{-1}$ respectively) and the infrared-absorption peaks of the polycaprolactone (at wavelengths equal to 2941, 2864, 1257 cm$^{-1}$ respectively).

The $^1$H-NMR spectra of the compound (4) was also measured to verify the structure thereof. This spectrum showed a signal at 7.5 ppm (having an integrated value A1, on the NMR spectra) and a signal at 7.9 ppm (having an integrated value A2), both of them corresponding to the aromatic protons of the benzotriazole ring. The signal at 2.3 ppm corresponding to the methylene protons near the carbon atoms of the polycaprolactone had an integration B. Since the value of B/(A1+A2) was equal to 5, the structure of the compound (4) was verified.

Figure 8:
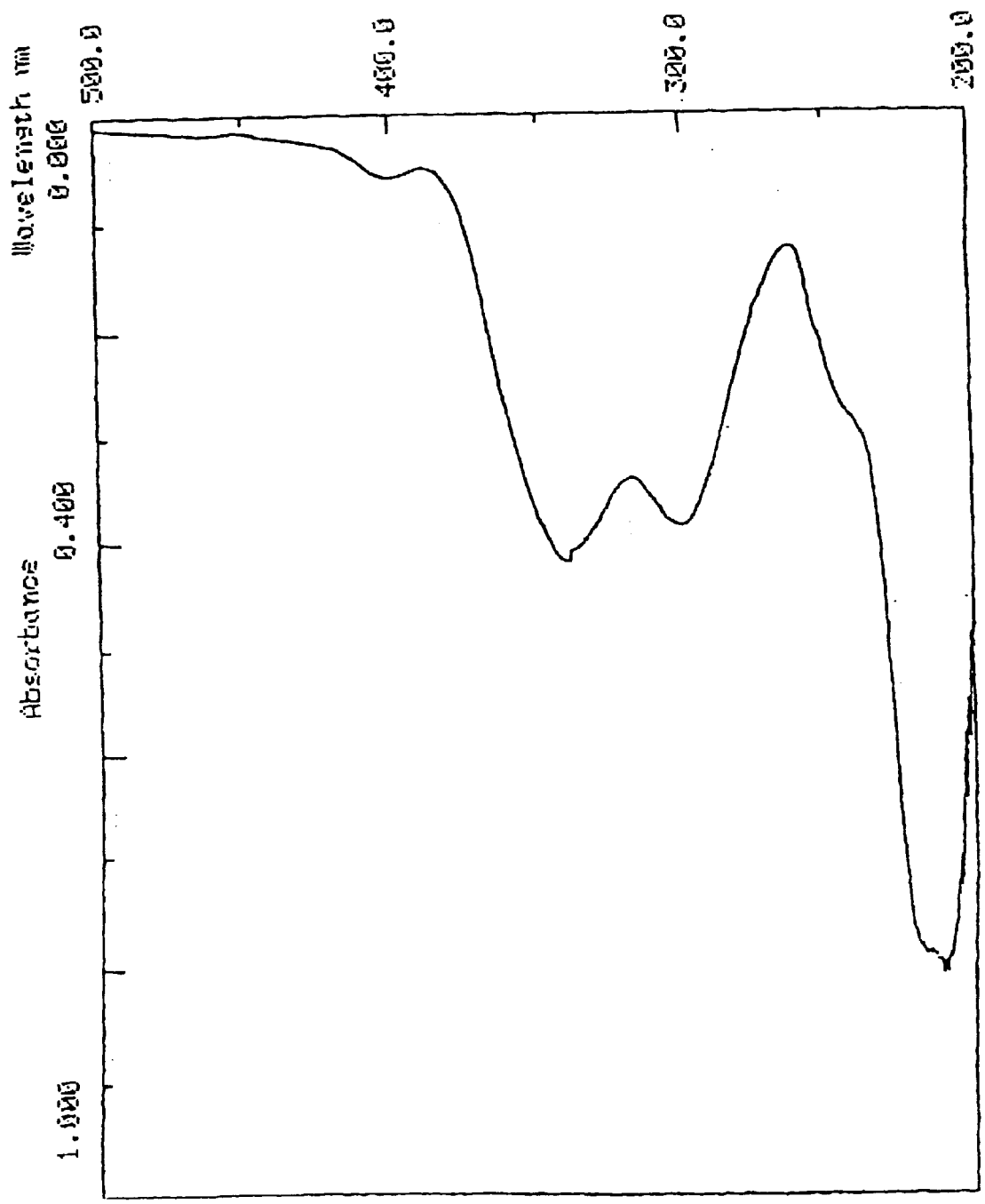
FIG. 8 is the ultraviolet and visible light-absorption spectrum of the compound (4) obtained in Synthesis Example 4.

10 mg of compound (4) were dissolved in 50 ml of chloroform. The ultraviolet-rays absorption spectrum of this compound was then measured using a quartz cell having a light pathway of 1 mm length. FIG. 8 shows the results of this experiment. According to FIG. 8, it was confirmed that the compound (4) had a sufficiently large ultraviolet-rays absorption in the ultraviolet range.

EXAMPLE 10 AND COMPARATIVE EXAMPLE 10

100 weight parts of polypropylene were mixed with the above-mentioned ultraviolet-rays absorbable polymers and with the prior art ultraviolet-rays absorbents. Table 9 shows the parts by weight of the ultraviolet-rays absorbents with respect to 100 parts by weight of polypropylene. The resulting mixtures were injection-molded to form dumbbells of JIS N°2.

TABLE 9

| | | Ultraviolet-rays absorbent | parts by weight |
|---|---|---|---|
| Example 10 | N°1 | compound obtained in Synthesis Example 3 | 2 |
| | N°2 | compound obtained in Synthesis Example 4 | 2 |
| Comparative | N°1 | trade name "MBEP" | 2 |
| Example 10 | N°2 | none | 0 |

Figure 9:
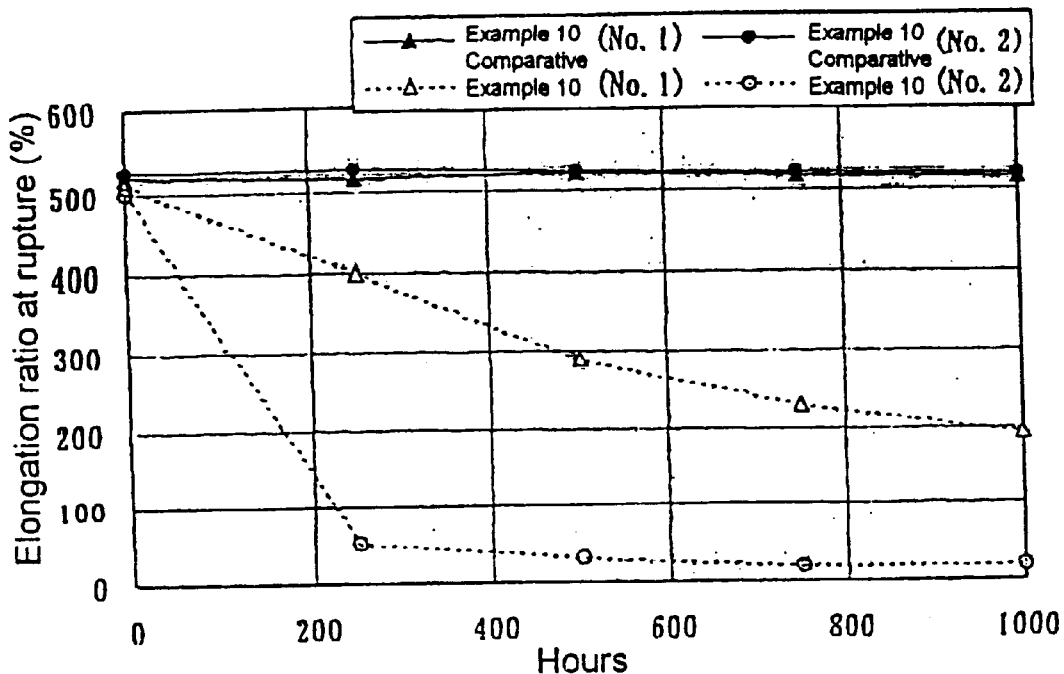
FIG. 9 is a graph showing the elongation ratio at rupture, after a light-exposure test, of the products of the prior art (Comparative Example 10) and the products of the present invention (Example 10), respectively.

The obtained dumbbells were submitted to the light-exposure test, using the sunshine weather-meter. After a determined time of exposure, a resistance test was performed in order to determine the corresponding elongation ratios at rupture. The experimental conditions were as explained hereinafter. FIG. 9 shows the results of these experiments. On the basis of FIG. 9, it was confirmed that the products of the invention had an excellent light resistance, compared with the products of the prior art.

EXAMPLE 11 AND COMPARATIVE EXAMPLE 11

100 parts by weight of polyvinyl-chloride were mixed with the above-mentioned ultraviolet-rays absorbable polymers and with the prior art ultraviolet-rays absorbents. Table 10 shows the parts by weight of the ultraviolet-rays absorbents with respect to 100 parts by weight of polyvinyl-chloride. The resulting mixtures were injection-molded to form plain plates having a thickness of 1.6 mm. The obtained plain plates were then submitted to the light-exposure test as in Example 10. The results of these experiments are shown in Table 10.

TABLE 10

| | | Ultraviolet-rays absorbent | parts by weight | light-exposure test |
|---|---|---|---|---|
| Example 11 | N°1 | compound obtained in Synthesis Example 3 | 1 | no color change after 2000 hours |
| | N°2 | compound obtained in Synthesis Example 4 | 1 | no color change after 2000 hours |
| Comparative Example 11 | N°1 | trade name "MBEP" | 1 | coloration after 1200 hours |
| | N°2 | none | 0 | coloration after 600 hours |

EXAMPLE 12 AND COMPARATIVE EXAMPLE 12

100 parts by weight of polyvinylidene-chloride were mixed with the above-mentioned ultraviolet-rays absorbable polymers and with the prior art ultraviolet-rays absorbents. Table 11 shows the parts by weight of the ultraviolet-rays absorbents with respect to 100 parts of polyvinylidene-chloride. The resulting mixtures were injection-molded to form plain plates having a thickness of 1.6 mm. The obtained plain plates were then submitted to the light-exposure test as in Example 10. The results of these experiments are shown in Table 11.

TABLE 11

| | | Ultraviolet-rays absorbent | parts by weight | light-exposure test |
|---|---|---|---|---|
| Example 12 | N°1 | compound obtained in Synthesis Example 3 | 1 | no color change after 2000 hours |
| | N°2 | compound obtained in Synthesis Example 4 | 1 | no color change after 2000 hours |
| Comparative Example 12 | N°1 | trade name "MBEP" | 1 | coloration after 950 hours |
| | N°2 | none | 0 | coloration after 400 hours |

EXAMPLE 13 AND COMPARATIVE EXAMPLE 13

100 parts by weight of polystryrene were mixed with the above-mentioned ultraviolet-rays absorbable polymers and with ultraviolet-rays absorbents of the prior art. Table 12 shows the parts by weight of ultraviolet-rays absorbents with respect to 100 parts by weight of polystryrene. The resulting mixtures were injection-molded to form plain plates having a thickness of 1.6 mm.

TABLE 12

| | | Ultraviolet-rays absorbent | parts by weight |
|---|---|---|---|
| Example 13 | N°1 | compound obtained in Synthesis Example 3 | 1 |
| | N°2 | compound obtained in Synthesis Example 4 | 1 |
| Comparative | N°1 | trade name "MBEP" | 1 |
| Example 13 | N°2 | none | 0 |

Figure 10:
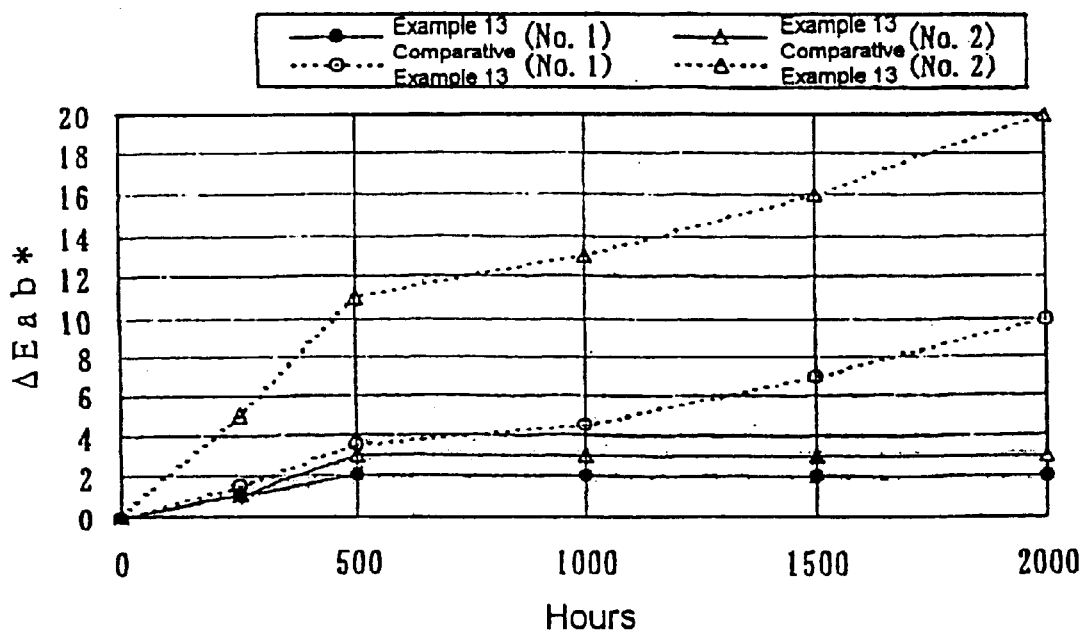
FIG. 10 is a graph showing the colour difference ($\Delta Eab^*$), after a light-exposure test, of the products of the prior art (Comparative Example 13) and the products of the present invention (Example 13), respectively.

The obtained plain plates were then submitted to the light-exposure test as in Example 10. Then, the colour difference (ΔEab*) of the surface of the plain plates was measured using a colorimeter (trade name: Colour Computer SM-2 manufactured by Suga Shikenki Co,. Ltd.). FIG. 10 shows the results of these experiments. According to FIG. 10, the products of the present invention had an excellent light resistance compared to the products of the prior art.

EXAMPLE 14 AND COMPARATIVE EXAMPLE 14

100 weight parts of a copolymer of acrylonitrile-butadiene-styrene were mixed with the above-mentioned ultraviolet-rays absorbable polymers and with the ultraviolet-rays absorbents of the prior art. Table 13 shows the parts by weight of the ultraviolet-rays absorbents with respect to 100 parts by weight of the acrylonitrile-butadiene-styrene copolymer. The resulting mixtures were injection-molded to form plain plates having a thickness of 1.6 mm.

TABLE 13

| | | Ultraviolet-rays absorbent | parts by weight |
|---|---|---|---|
| Example 14 | N°1 | compound obtained in Synthesis Example 3 | 1 |
| | N°2 | compound obtained in Synthesis Example 4 | 1 |
| Comparative Example 14 | N°1 | trade name "MBEP" | 1 |
| | N°2 | none | 0 |

Figure 11:
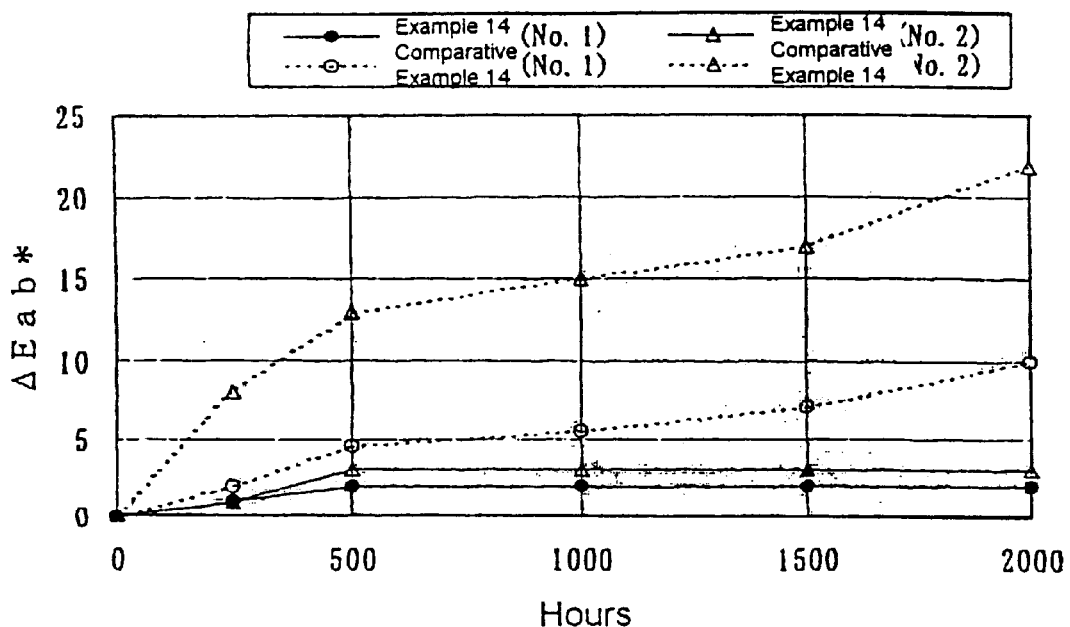
FIG. 11 is a graph showing the colour difference ($\Delta Eab^*$), after a light-exposure test, of the products of the prior art (Comparative Example 14) and the products of the present invention (Example 14), respectively.

The obtained plain plates were then submitted to the light-exposure test as in Example 10. Then, the colour difference ($\Delta Eab^*$) of the surface of the plain plate was measured using a colorimeter (trade name: Colour Computer SM-2 manufactured by Suga Shikenki Co,. Ltd.). FIG. 11 shows the results of these experiments. According to FIG. 11, it was confirmed that the products of the present invention had an excellent light resistance compared with the products of the prior art.

EXAMPLE 15 AND COMPARATIVE EXAMPLE 15

100 parts by weight of polycarbonate were mixed with the above-mentioned ultraviolet-rays absorbable polymers and with the ultraviolet-rays absorbents of the prior art. Table 14 shows the parts by weight of the ultraviolet-rays absorbents with respect to 100 parts by weight of polycarbonate. The resulting mixtures were injection-molded to form plain plates having a thickness of 1.6 mm.

TABLE 14

| | | Ultraviolet-rays absorbent | parts by weight |
|---|---|---|---|
| Example 15 | N°1 | compound obtained in Synthesis Example 3 | 1 |
| | N°2 | compound obtained in Synthesis Example 4 | 1 |
| Comparative Example 15 | N°1 | trade name "MBEP" | 1 |
| | N°2 | none | 0 |

Figure 12:
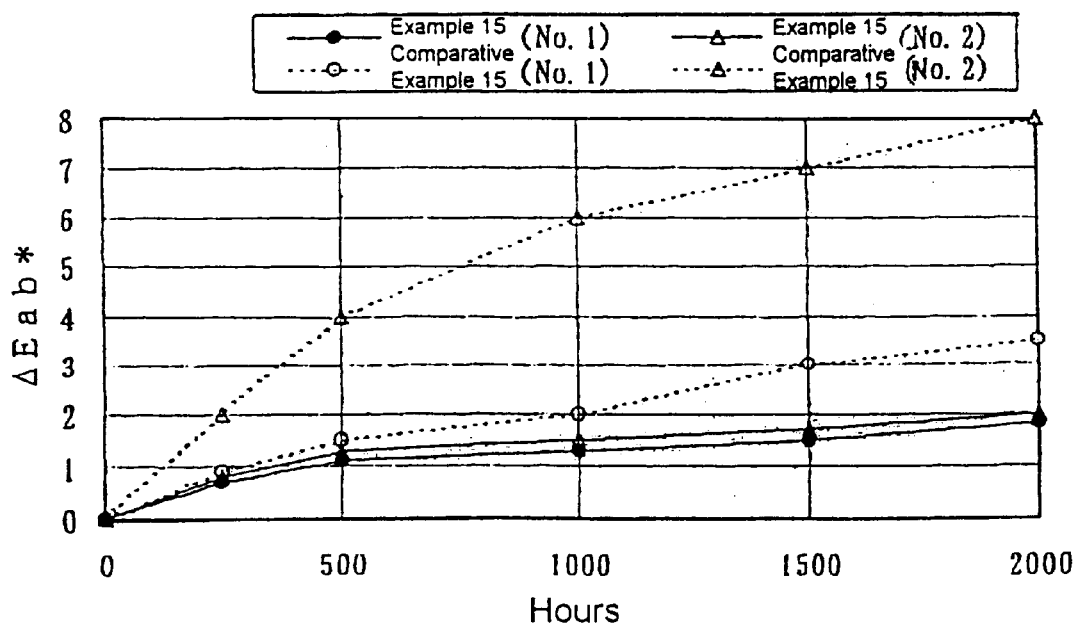
FIG. 12 is a graph showing the colour difference ($\Delta Eab^*$) after a 30 light-exposure test, of the products of the prior art (Comparative Example 15) and the products of the present invention (Example 15), respectively.

The obtained plain plates were then submitted to the light-exposure test as in Example 10. Then, the colour difference ($\Delta Eab^*$) of the surface of the plain plate was measured using a colorimeter (trade name: Colour Computer SM-2 manufactured by Suga Shikenki Co,. Ltd.). FIG. 12 shows the results of this experiment. According to FIG. 12, it was confirmed that the compositions using the ultraviolet-rays absorbents of the present invention had an excellent light resistance compared with the compositions using the ultraviolet-rays absorbents of the prior art.

EXAMPLE 16 AND COMPARATIVE EXAMPLE 16

The ultraviolet-rays absorbable compounds obtained in the above-mentioned Synthesis Examples and the ultraviolet-rays absorbents of the prior art were mixed with polystyrene and then dissolved in tetrachloroethane in order to form an homogenous solution. Table 15 shows the amount by weight of the ultraviolet-rays absorbent and the polystyrene, respectively for each solution. The resulting solution was dropped on a quartz-glass disk having a thickness of 1 mm and a diameter of 30 mm, to form a thin homogenous film having a thickness of 0.9–1.0 µm, by use of a spin coater. The disk was then introduced in 70° C. hot water and the absorbance at 340 nm thereof was measured every two hours.

TABLE 15

| | Ultraviolet-rays absorbent | parts by weight (mg) | up:A0 down:A10 | retention rate (%) |
|---|---|---|---|---|
| Example 16 | compound obtained in Synthesis Example 3 polystyrene | 100 900 | 0.320 0.318 | 99.3 |
| Comparative Example 16 | trade name "MBEP" polystyrene | 100 900 | 0.325 0.243 | 74.8 |

In the case of the ultraviolet-rays absorbents of the prior art (Comparative Example 16), the absorbance decreased linearly due to the elution of the ultraviolet-rays absorbent. On the contrary, in the case of the compound synthesised in Example 3 (Example 16, ultraviolet-rays absorbent of the invention), there was no elution or bleeding of the ultraviolet-rays absorbent and thus the absorbance kept the same value as initially. Table 15 shows the initial absorbance at 340 nm ($A_0$) and the absorbance at 340 nm after 10 hours ($A_{10}$). The ratio $A_0/A_{10}$ is indicated in Table 15.

After 10 hours, the disks were submitted to the light-exposure test as explained in Example 10. The disk obtained in Example 16 was exposed for 500 hours without any eye-visible colour change. However, the disk obtained in the comparative Example 16 showed a yellowing after 200 hours of light exposure. Consequently, it was confirmed that the compositions of the invention had a stable light resistance.

EXAMPLE 17 AND COMPARATIVE EXAMPLE 17

The ultraviolet-rays absorbable compounds obtained in the above-mentioned Synthesis Example 4 and the ultraviolet-rays absorbents of the prior art were mixed with poly(methyl methacrylate) (PMMA) and dissolved in tetrachloroethane to form a homogenous solution. Table 16 shows the amount by weight of the ultraviolet-rays absorbents and the PMMA, respectively. The resulting solution was used, as in Example 16, to form a homogeneous film having a thickness of about 1 µm. The disk was then introduced in 70° C. hot water and the absorbance at 340 nm thereof was measured every two hours. Table 16 shows the results of this experiment.

TABLE 16

| | Ultraviolet-rays absorbent | parts by weight (mg) | up:A0 down:A10 | retention rate (%) |
|---|---|---|---|---|
| Example 17 | compound obtained in Synthesis Example 3 PMMA | 150 850 | 0.468 0.458 | 97.9 |
| Comparative Example 17 | trade name "MBEP" PMMA | 100 900 | 0.430 0.079 | 18.4 |

On the basis of the results shown in Table 16, it can be proved that the ultraviolet-rays absorbents of the invention were completely maintained within the matrix of the resin and consequently, it was confirmed that there was quite no elution and no bleeding of the ultraviolet-rays absorbent of the invention.

EXAMPLE 18 AND COMPARATIVE EXAMPLE 18

15 mg of the ultraviolet-rays absorbable polymer obtained in Synthesis Example 4 were mixed with 85 mg of polyethylene terephthalate (Example 18). Separately, 5 mg of a ultraviolet-rays absorbent of the prior art (2-(2'-hydroxy-5'-methyl-phenyl)benzotriazole were mixed with 95 mg of polyethylene terephthalate (Comparative Example 18). These mixtures were used to form films as in Example 16. The obtained films were introduced into a 2% sodium hydroxide aqueous solution which is at 70° C. The absorbance (At) of these films was measured at 340 nm and 231 nm every two hours. The retention ratio was defined as At/Ao. After 10 hours, the absorbance and the retention ratio of the films were measured. In the case of polyethylene terephthalate film without any ultraviolet-rays absorbent, there was a remarkable dissolution of the polyethylene terephthalate film (there was a decrease of 50% of the lasting rate at 231 nm). In the case of the polyethylene terephthalate film containing an ultraviolet-rays absorbent of the prior art, there was also a remarkable bleeding of the ultraviolet-rays absorbent, in addition to the above-mentioned dissolution of the film (there was a decrease of 85% of the retention ratio at 340 nm). However, the retention ratio was always maintained to about 100% in the case of Example 18.

We claim:

1. A polyester or ester compound having a benzotriazole group, of formula (1) or (1')

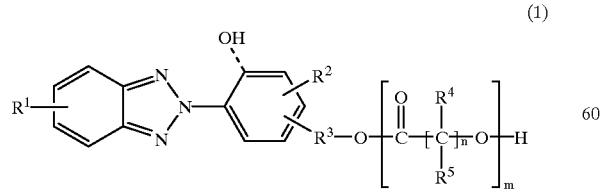
(1)

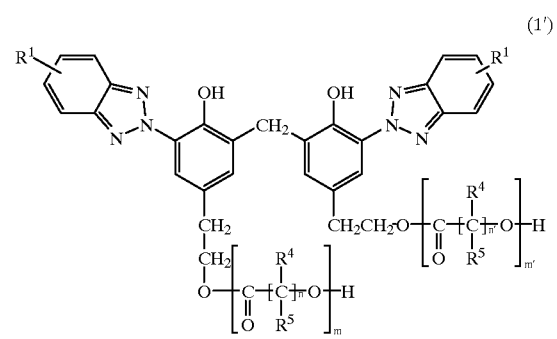
(1')

wherein $R^1$ is hydrogen atom, halogen atom or an alkyl group having 1 to 10 carbon atoms;

$R^2$ is hydrogen atom or an alkyl group having 1 to 10 carbon atoms;

$R^3$ is an alkyl group having 1 to 10 carbon atoms;

$R^4$ to $R^5$ are a hydrogen atom or an alkyl group having 1 to 10 carbon atoms;

n is an integer of 4–8;

m is a number of 1–20.

2. A method of synthesizing a compound according to claim 1, characterized in that a compound of formula (2) or (2') is allowed to react with a lactone compound of formula (3) resulting in a ring opening of the lactone (3) compound

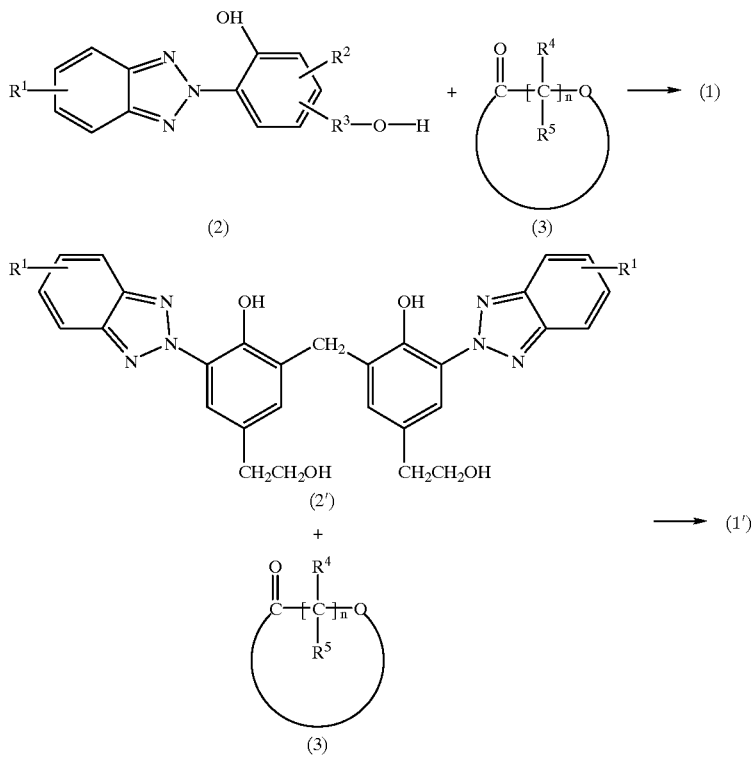

wherein:

- $R^1$ is hydrogen atom, halogen atom or an alkyl group having 1 to 10 carbon atoms;
- $R^2$ is hydrogen atom or an alkyl group having 1 to 10 carbon atoms;
- $R^3$ is an alkyl group having 1 to 10 carbon atoms;
- $R^4$ to $R^5$ are a hydrogen atom or an alkyl group having 1 to 10 carbon atoms;
- n is an integer of 4–8;
- m is a number of 1–20.

3. An ultraviolet-rays absorbent characterised in that it comprises a polyester or ester compound according to claim 1 or obtained by the method of claim 2.

4. A resin composition characterised in that it contains a synthetic resin and an ultraviolet-rays absorbent according to claim 3.

5. The resin composition according to claim 4, characterised in that said synthetic resin contains at least one kind of resin selected from the group consisting of a polyvinyl-chloride, a polyvinylidene-chloride, a polyolefin, a polycarbonate, a polystyrene, an acrylic resin, a methacrylic resin, a polyamide, a polyester, an acrylonitrile-butadiene-styrene resin and a thermoplastic urethane resin.

* * * * *